(12) United States Patent
Aneja

(10) Patent No.: US 6,737,536 B1
(45) Date of Patent: May 18, 2004

(54) INOSITOLPHOSPHOLIPIDS AND ANALOGUES

(75) Inventor: Rajindra Aneja, Ithaca, NY (US)

(73) Assignee: Nutrimed Biotech, Ithaca, NY (US)

( * ) Notice: Subject to any disclaimer, the term of this patent is extended or adjusted under 35 U.S.C. 154(b) by 142 days.

(21) Appl. No.: 10/067,648

(22) Filed: Feb. 4, 2002

Related U.S. Application Data

(60) Provisional application No. 60/266,433, filed on Feb. 5, 2001.

(51) Int. Cl.⁷ .................................................. C07F 9/02
(52) U.S. Cl. .............................. 554/82; 554/79; 558/91
(58) Field of Search ........................ 554/79, 82; 588/91

(56) References Cited

U.S. PATENT DOCUMENTS 6,096,916 A * 8/2000 Anja ........................... 558/91

* cited by examiner

Primary Examiner—Deborah D. Carr
(74) Attorney, Agent, or Firm—Williams, Morgan and Amerson

(57) ABSTRACT

This invention relates to inositolphospholipids, particularly to synthetic phosphatidyl-myo-inositols (PtdIns), ceramide-phosphoinositols (CerPhosIns) and their structural and stereochemical analogues. The invention specifically provides a novel approach to synthesis of inositolphospholipids which is suitable for laboratory scale preparation as well as for large scale industrial production. The synthetic approach is applicable equally well for the preparation of inositolphospholipids carrying saturated lipid chains, unsaturated lipid chains with one or more double or triple bonds, chains with hydroxyl, amino and other functional groups, or combinations of these. In addition, it provides novel high purity diastereomer molecular species of inositolphospholipids that have unequivocally defined structure and absolute stereochemistry in both the myo-inositol and the glycerol residues and are obtainable only by the present new approach. The invention further provides methods for characterizing and using these high purity diastereomeric compounds.

8 Claims, No Drawings

INOSITOLPHOSPHOLIPIDS AND ANALOGUES

The present application claims priority to provisional application Ser. No. 60/266,433, filed Feb. 5, 2001.

The present invention was partially made with funds provided by the Department of Health and Human Services under Grant No. NIH GM59550. Accordingly, the United States Government owns certain rights in this invention.

BACKGROUND OF THE INVENTION

1. Field of the Invention

Inositolphospholipids are conjugates of a lipid and a myo-inositol linked by a phosphodiester bridge. This phospholipid group and the derived glycosylates and phosphates occur as minor components of biological cells, and are involved in vital cellular functions including intracellular signaling. Two biochemical parents are the phosphatidyl-myo-inositols (PtdIns) and the ceramide-phosphoinositols (CerPhosIns). The present invention concerns synthetic PtdIns, CerPhosIns and their structural and stereochemical analogues. It is not concerned with their glycosylated or phosphorylated derivatives. The invention specifically provides a novel approach to synthesis of inositolphospholipids which is suitable for laboratory scale preparation as well as for large scale industrial production. The synthetic approach is applicable equally well for the preparation of inositolphospholipids carrying saturated lipid chains, unsaturated lipid chains with one or more double or triple bonds, chains with hydroxyl, amino and other functional groups, or combinations of these. In addition, it provides novel high purity diastereomer molecular species of inositolphospholipids that have unequivocally defined structure and absolute stereochemistry in both the myo-inositol and the glycerol residues and are obtainable only by the present new approach. The invention further provides methods for characterizing and using these high purity diastereomeric compounds. The synthetic products have utility, inter alia, as biochemical reagents in studies on the structure and function of cell membranes and mechanisms of intracellular signaling, as reference compounds for analysis of cellular inositolphospholipids, as substrates in assays and diagnostics kits for enzymes involved in signaling via the inositolphospholipids, as lead compounds for the design and development of novel drugs for the treatment of disorders caused by aberrant signaling including diabetes and some cancers, for biodelivery of specific pharmacodynamic fattyacyls covalently incorporated in the inositolphospholipid structure, as the lipid component in liposomal delivery vehicles for cytotoxic drugs, bioactive peptides, proteins and polynucleotides, and in cosmetics formulations.

2. Description of Related Art

Inositolphospholipids: Structures, Biological Roles, and Utility

Inositolphospholipids constitute an important group of biological small molecules which includes PtdIns and CerPhosIns (Carter et al., 1965). Cellular PtdIns belong to the 1D-1-myo-inositol series and have the 1D-1-(1-fattyacyl'-2-fattyacyl$^2$-sn-glycero-3-phospho)-myo-inositol absolute stereochemical structure. In the radyl analogues (Radyl-PtdIns), the 1-fattyacyl residue is replaced by O-alkyl, and in CerPhosIns, the 1,2-diacylglycero residue is replaced by a ceramide moiety. The corresponding lyso-series of inositolphospholipids lack the 2-fattyacyl or, and thus have a free hydroxyl group at the glycero-2 position. The sphingosyl-phosphoinositols (Sphingosyl-PhosIns) lack the amide fattyacyl and have a free 2-amino group which may be derivatized further. Representative structures of the cellular series follow.

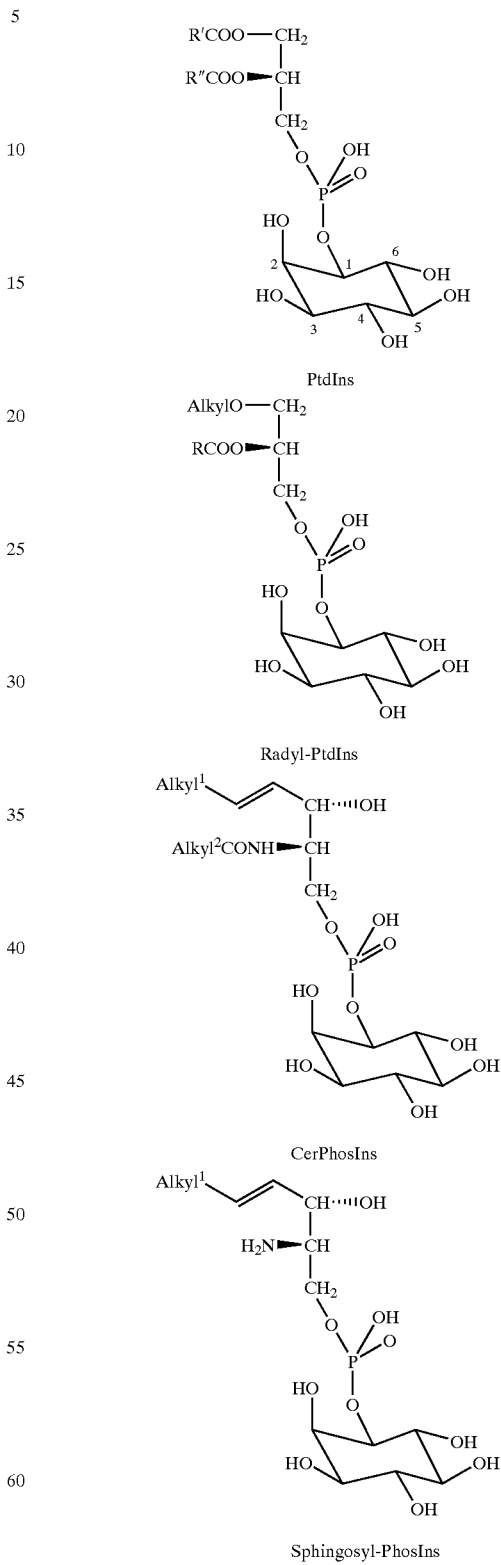

PtdIns

Radyl-PtdIns

CerPhosIns

Sphingosyl-PhosIns

As noted above, in cellular PtdIns the inositol moiety is in the 1D-1-myo-inositol and the glycerol moiety is in the sn-glycero-3-phospho configuration. The glycero residue is esterified with mixtures of saturated long carbon chain fattyacyls, and unsaturated and polyunsaturated fattyacyls collectively referred to as (poly)unsaturated fattyacyls. Thus PtdIns in natural phospholipids are complex mixtures of molecular species differing in their fattyacyl composition and distribution between glycero-1 and -2 positions. In the naturally occurring CerPhosIns series, the sphingosine/ceramide residue has the D-erythro stereochemical configuration. CerPhosIns show variable chain length and degree of unsaturation in the two alkyl groups of the ceramide residue, and may carry additional unsaturation, hydroxyl or related functional groups. Synthetic PtdIns analogues are based on the sn-glycero-3-phospho as well as the sn-glycero-1-phospho configurations, and the synthetic analogues of CerPhosIns are based on the D-erythro, L-erythro, D-threo, or L-threo stereochemical configurations in the sphingosine/ceramide residues. Diastereomers are formed by all combinations of the 1D-1- and 1L-1-myo-inositols with the aforementioned glycerol or sphingosine/ceramide configurations.

In eukaryotic cells, PtdIns are quantitatively minor but vital components of membrane lipids with critical structural and metabolic roles. In the structural role, PtdIns function akin to the more abundant phosphatidylcholines and phosphatidylethanolamines in membranes (Small, 1986) but this has not been studied in detail. In its metabolic roles, PtdIns is the parent participant in the vital PtdIns cycle which is responsive directly to various extracellular stimuli acting on the cell (Hokin, 1985). Agonist stimulated metabolism is mediated by combinations of many regulatory protein and enzyme families including the PtdIns transfer protein, PtdIns synthase, and phospholipases, kinases and phosphate-phosphatases specific for the PtdIns group implicated in intracellular signaling. Mono, bis, and trisphosphates of PtdIns are formed and their cellular concentrations are regulated by the actions of kinase and phosphate-phosphatase groups of enzyme families which are specific for the 3-, 4-, or 5-positions. The action of PtdIns specific phospholipase C (Rhee et al., 1989) on PtdIns-4,5-bisphosphate generates the intracellular second messengers inositol-1,4,5-trisphosphate and diacylglycerol which respectively mediate release of intracellular Ca ions (Berridge, 1984, 1987, 1993) and activation of protein kinase C (Nishizuka, 1986) respectively. The 3-phosphate series (Whitman et al., 1988) act as messengers in mitogenic and related signals more directly (Toker et al., 1994; Duckworth and Cantley, 1996). Action of cytosolic phospholipase $A_2$ liberates arachidonic acid from the sn-glycero-2-O-acyl moiety (Lapetina et al, 1981) which is utilized in the arachidonic acid-eicosanoid messenger cascades. Thus PtdIns is a direct and indirect reservoir of additional signaling molecules which mediate and control vital cellular functions (Bell et al., 1996). PtdIns moiety is the lipid component in glycosyl-phosphatidylinositols which function as membrane anchors of important cellular proteins (Englund, 1993), and as transducers in the insulin messenger cascade (Saltiel et al., 1986). The radyl and sphingo analogues of PtdIns and glycosyl-phosphatidylinositols have similar and additional roles (Ferguson and Williams, 1988).

Synthetic inositolphospholipids and analogues are required as research reagents in multifarious signaling and related biomedical fields some of which are summarized in section "Field of the Invention" and are further discussed below.

PtdIns as the amphiphile in liposomal drug delivery vehicles prevents recognition of vesicle surface by the phagocytic cells of the reticuloendothelial system, the circulating mononuclear phagocytic cells, and those located in liver and spleen, and enhances blood circulation time of the drug formulation (Lee et al., 1992).

PtdIns in tissues are mixtures of molecular species, mostly with saturated fattyacyls at the 1-glycero and polyunsaturated fattyacyls at the 2-glycero positions. In early studies, development of therapeutics was linked to the action of cytosolic phospholipase $A_2$ and the liberation of arachidonic acid from animal tissue derived PtdIns, and of linoleic and linolenic acids from plant derived PtdIns. These studies could not be pursued to definitive conclusions because methods of synthesis and consequently well defined synthetic PtdIns with selected (poly)unsaturated fatty acids were not available. However, very promising results were obtained using plant versus animal tissue derived PtdIns. Plant PtdIns was reported to have antiviral activity and recommended as a prophylactic for HIV; the identity of the fattyacyl in the sn-glycero-2-O-position appears critical for activity (Jett-Tilton, 1991). Plant PtdIns has a dramatic toxic effect on numerous tumor cells lines but not on normal cells, while animal PtdIns stimulates cell growth for both cell types. The difference between the PtdIns types may be attributed to the fattyacyl composition, particularly at the sn-glycero-2-O position (Jett et al., 1985).

More recently, attention has focused on developments based on inhibitors and modulators of the phospholipases, kinases, and phosphate phosphatases involved in signal transduction. PtdIns analogues modified in the inositol-2-position, for instance the 2-fluorodeoxy-scyllo-inositol types, were found to be effective inhibitors of phospholipase C and potent anti-inflammatory and analgesic agents (Yang et al., 1985). 2-Modified phosphoinositides in general have analogous potential as lead compounds for the development of therapeutics relying on the inhibition of PtdIns-specific phospholipase C (PI-PLC) (Aneja and Aneja, 1999). Other inhibitors of PI-PLC are based on the thiophosphate and phosphonate analogues. The water soluble D-myo-inositol 4-(hexadecyloxy)-3(S)methoxy-butane-phosphonate, a phosphonate tar analogue of PtdIns, is reported to inhibit epithelial cell proliferation (Leung et al., 1998a). PtdIns analogues modified at the inositol-3-position inhibit the growth of mammalian cells, and have potential for treating neoplastic conditions and other proliferative disorders (Kozikowski et al., 1993). Inhibitors of ceramide-phosphoinositol synthase are potent antifungal agents (Mandala et al., 1998).

Research activity in signaling via PtdIns and derived lipids has been increasing tremendously during the last two decades. Thus significant quantities of inositolphospholipids are required for this and for other applications including in drug delivery vehicles, but are not available because appropriate synthetic methodology for large scale production is not available.

Literature Methods for Synthesis of Inositolphospholipids

Synthesis of inositolphospholipids reported in the prior art are largely directed at the synthesis of PtdIns. Early work during 1970–75 advanced the PtdIns synthesis art, but did not result in a practical approach (reviewed in Gigg, 1980). Interest in synthesis was renewed when the critical role of PtdIns and derived phosphates in intracellular signaling was recognized. Several syntheses of PtdIns have been reported in the last 10 years (Aneja et al., 1989; Jones et al., 1989; Salamonczyk and Bruzik, 1990; Young et al., 1990; Lewis et al., 1993; Rebecchi et al., 1993; Leung et al., 1998b).

The chemical syntheses are all based on broad retrosynthetic dissection of PtdIns into fatty acid, phosphoric acid, sn-glycerol and myo-inositol synthons, and synthesis from these synthons by regio- and enantio-specific reesterifications or equivalent chemical or enzyme catalyzed reactions. Regioselectivity is achieved via selective temporary O-protection. Both glycerol and myo-inositol are meso structures which form enantiomeric pairs (racemates) by appropriate O-substitution, for instance by temporary O-protecting groups introduced regioselectively to create optically active synthons. These racemates must be separated into individual enantiomers. Methods for the requisite separation include chiral phase chromatography, enantiospecific hydrolysis or transesterification using enzyme catalysis, or by physical separation of diastereomers of myo-inositol derivatives in salt or covalent bonds with chiral ligands. The individual enantiomers can be obtained also by synthesis of myo-inositols from other chiral natural products, or by asymmetric synthesis from non-chiral materials (Billington, 1993). Corresponding methods are available also for O-substituted glycerols. Synthesis relying on enantiospecific transphosphatidylation with 1-D-myo-inositol catalyzed by phospholipase D has been claimed albeit without adequate proof (Mandal et al., 1980), and, regiospecificity of lipase (Aneja et al., 1989) and phospholipase $A_2$ (Somerharju et al., 1985; Aneja et al., 1989) enzyme catalyzed hydrolysis in the diacylglycerol moiety of PtdIns derivatives has been utilized in partial synthesis from natural PtdIns. In all methods to date, selective O-protection, enantiomer resolution and the requisite ancillary steps are required and add significantly to the complexity and cost of synthesis.

Obtaining the individual enantiomeric myo-inositol synthons in high enantiomeric optical purity and assignment of absolute configuration to either the 1-D-myo-inositol or 1-L-myo-inositol series has been problematic. It was recognized and established only recently (Aneja et al., 1994, 1995) that literature preparations of two critical synthons for inositolphospholipids, namely optically resolved 2,3,4,5,6-pentabenzyl-myo-inositols and 2,3:5,6-dicyclohexylidene-myo-inositois, had a low enantiomeric purity, and the assigned absolute configurations were incorrect. Further, it was concluded (Aneja and Aneja, 2000) that previous synthetic PtdIns prepared from these synthons were mixtures of diastereomers and that the absolute configuration of the major PtdIns component was identified incorrectly.

Prior art methods of synthesis of PtdIns have disadvantages inherent in their choice of strategies, reagents and protocols for formation of the phosphodiester bond of PtdIns. In general, literature syntheses create a phosphotriester as precursor intermediate for the phosphodiester bond in one of two ways. Some syntheses employ pentavalent phosphorus reagents which carry a protecting group, usually a phenyl group, that must be removed by catalytic hydrogenolysis to generate the requisite phosphodiester (Young et al., 1990). Hydrogenolysis of phenyl-phosphates causes concomitant reduction of (poly)unsaturated fattyacyl, and of unsaturated bonds in sphingo and related moieties. Most prior art syntheses employ trivalent phosphorus reagents and initially create a phosphite or equivalent intermediate which is then oxidized to the phosphotriester and the latter deprotected to the required phosphodiester. In these syntheses, the reagents and protocols for oxidation damage unsaturated and related groups, particularly (poly)unsaturated fattyacyls.

Thus most prior art methods are suitable only for the syntheses of inositolphospholipids with saturated fattyacyl or saturated sphingo residues. In addition, most prior art syntheses are limited to use of benzyl as the O-protecting group for myo-inositol hydroxyls and its ultimate removal by catalytic hydrogenolysis. The use of acetyl as O-protecting group (Molotkovsky and Bergelson, 1973; Aneja et al., 1989) overcomes these deficiencies but creates others because deprotection by hydrazinolysis of O-acetyl protected PtdIns intermediates causes extensive concomitant loss of fattyacyls, with consequent difficulties in product purification and variable low yields. The results and analysis underscore the inadequacies of the relevant prior art and emphasize the need for better synthetic methodology suitable both for saturated and (poly)unsaturated type inositolphospholipids. The approach of the present invention meets these needs, and in addition employs inexpensive protecting groups, low cost reagents, new high-yield protocols, and is scalable for economic large scale production.

Lack of Criteria for Structural and Steoreochemical Configuration of PtdIns

It was stated above that all cellular inositolphospholipids belong to the 1D-1-(phospho)-myo-inositol series, and that cellular PtdIns have the 1D-1-(1-fattyacyl'-2-fattyacyl$^2$-sn-glycero-3-phospho)-myo-inositol absolute stereochemical structure. Synthetic analogues of PtdIns, wherein both the myo-inositol and the glycerol residues are in optically active form, constitute a set of four diastereomers comprising 1D-1-(1-fattyacyl$^1$-2-fattyacyl$^2$-sn-glycero-3-phospho)-myo-inositol, 1D-1-(3-fattyacyl$^1$-2-fattyacyl$^2$-sn-glycero-1-phospho)-myo-inositol, 1L-1-(1-fattyacyl$^1$-2-fattyacyl$^2$-sn-glycero-3-phospho)-myo-inositol, and 1L-1-(3-fattyacyl$^1$-2-fattyacyl$^2$-sn-glycero 1-phospho)-myo-inositol. Normally, such diastereomers can be characterized and their stereostructures correlated by a combination of specific rotation $[\alpha]_D$ and nuclear magnetic resonance spectra (NMR).

The preparation of one set of four PtdIns diastereomers wherein both fattyacyl$^1$ and fattyacyl$^2$ equal hexadecanoyl residue, has been reported (Young et al., 1990); in this case, the four products showed no significant differences in proton and phosphorus NMR spectra. It is puzzling that in spite of inability to distinguish the PtdIns diastereomers by NMR alone, the optical rotation data were not reported for any diastereomer. Thus the only publication which describes the full set of PtdIns diastereomers, albeit with just one specific fattyacyl, does not provide adequate characterization for distinguishing diastereomers and for relating absolute stereochemical structure to measurable physical properties. In related work on one pair of synthetic PtdIns (Garigapati and Roberts, 1993), identical NMR spectra and $[\alpha]_D$ values+ 14.2 and −13.9 respectively were observed for diheptanoyl-sn-glycero-3-phospho-D-myo-inositol and diheptanoyl-sn-glycero-3-phospho-L-myo-inositol. We have shown that the PtdIns reported by Garigapati and Roberts are not diastereomers with the aforementioned stereochemical structures but rather are enantiomers wherein the glycero-residue is racemic. Overall, the stereochemical structures and absolute configurations claimed for the aforementioned and related literature products have not been proven, inter alia, for lack of suitable methodology. The present invention provides such methodology for PtdIns diastereomers.

SUMMARY OF THE INVENTION

The present invention concerns inositolphospholipids, as well as their synthetic structural and stereochemical analogues. Thus, this invention concerns inositolphospholipids, particularly phosphatidyl-myo-inositols (PtdIns), their radyl and sphingo analogues with the core structure and stereochemistry identical with that of the cellular inositolphospholipids, and stereo-structural isomers of the aforementioned species. It specifically provides a novel approach to synthesis of inositolphospholipids and analogues which is suitable for laboratory scale preparation as well as large scale industrial production. The synthetic approach is applicable for the preparation of inositolphospholipids carrying saturated chain lipids as well as lipid chains carrying functional groups which may include but are not limited to one or more double or triple bonds. The key reaction step in synthesis is the direct condensation to form the requisite phosphodiester bond between the 1-hydroxyl of a selectively O-protected myo-inositol and a lipid-phosphoric acid. A novel protocol giving very high yield is provided for this condensation. The synthesis is exemplified by the preparation of several inositolphospholipids including 1D-1-(1-stearoyl-2-arachidonyl-sn-glycero-3-phospho)-myo-inositol and CerPhosIns.

The invention further provides novel high purity diastereomer molecular species of inositolphospholipids that have unequivocally defined structure and absolute stereochemistry in both the myo-inositol and the glycerol residues. The resulting pure diastereomer products are obtainable only as prepared now by the new approach of the present invention. Criteria for establishing diastereomer purity and correlating stereochemical structure and absolute configuration to physical properties of diastereomers have not been available. This invention provides such criteria, and these criteria are based on comparison of molar rotations using data for natural PtdIns as the bench-mark for the 1D-1-(1-fattyacyl$^1$-2-fattyacyl$^2$-sn-glycero-3-phospho)-myo-inositol absolute stereochemical structure. The invention also provides inositolphospholipids with many structural variations in the lipid residue, including chains with double and triple bonds, with hydroxyl, amino and other functional groups, or combinations of these, and these novel products have utility in research and industry.

DETAILED DESCRIPTION OF THE INVENTION

The novel approach to synthesis of inositolphospholipids is described, followed by methodology for characterization of the products and correlating stereochemical structure with physicochemical properties, and the synthetic products of this invention with their utility.

The Novel Approach to Synthesis of Inositolphospholipids

The present approach (Scheme 1) is a novel convergent synthesis wherein a lipid and a selectively O-protected myo-inositol synthon are prepared, condensed together to form an O-protected inositolphospholipid, and the O-protecting groups removed to generate the target inositolphospholipid. The lipid synthon is a lipid-monophosphoric acid. The selectively O-protected optically resolved myo-inositol synthon is chosen wherein at least the 1-equatorial hydroxyl is unprotected (free), the 3-hydroxyl and at least three other hydroxyls carry identical or non-identical temporary O-protecting groups. The condensation creates a covalent phosphodiester link forming a selectively O-protected derivative of the target inositolphospholipid. Removal of all O-protection generates the target inositolphospholipid. The approach outlined in Scheme 1 is for PtdIns but is applicable to all inositolphospholipids.

Scheme 1: Approach to synthesis illustrated for 1D-1-(1,2-diacyl-sn-glycero-3-phospho)-myo-inositol diastereomer.

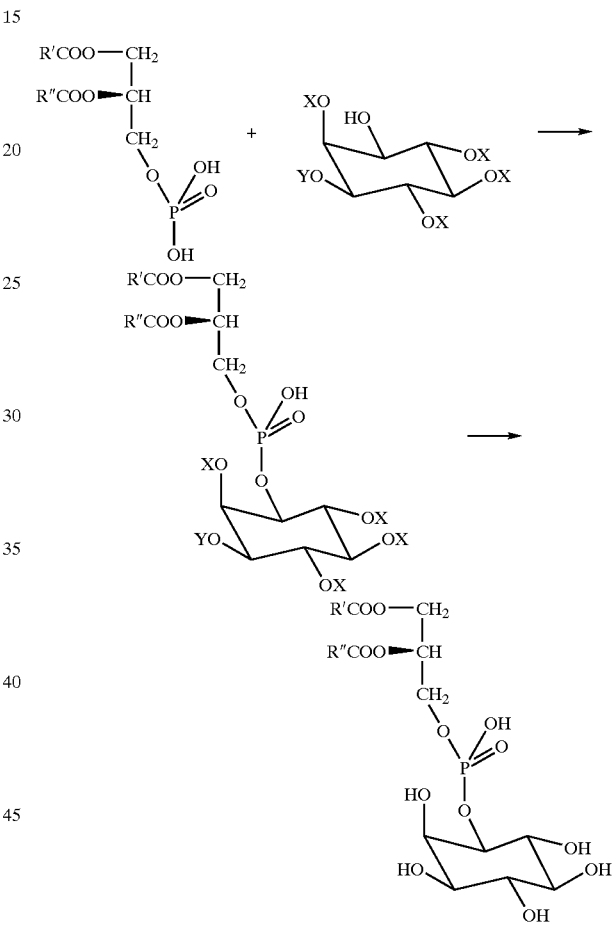

X = O-protecting group or H, but not phosphate or O-protected phosphate, or glycosyl or O-protected glycosyl;

Y = O-protecting group, but not phosphate or O-protected phosphate, or glycosyl or O-protected glycosyl;

R'CO, R"CO = Fattyacyl (saturated or unsaturated).

Lipid Synthons: Lipid-phosphoric acids are the preferred lipid synthons. The chiral lipid-phosphoric acid synthons represented by the phosphatidic acid 1-stearoyl-2-arachidonyl-sn-glycero-3-phosphoric acid 1 (Scheme 2) and its enantiomer 3-stearoyl-2-arachidonyl-sn-glycero-1-phosphoric acid 2 (structure not shown) were prepared from the corresponding n-butyl esters by lipolysis with phospholipase D (PLD) as outlined in Scheme 2. Other methods for synthesis of lipid-phosphoric acids are available in the literature and may be utilized. The cited background literature is incorporated herein by reference.

Scheme 2: Synthesis of 1-O-stearoyl-2-O-arachidonyl-sn-glycero-3-phosphoric acid (5).

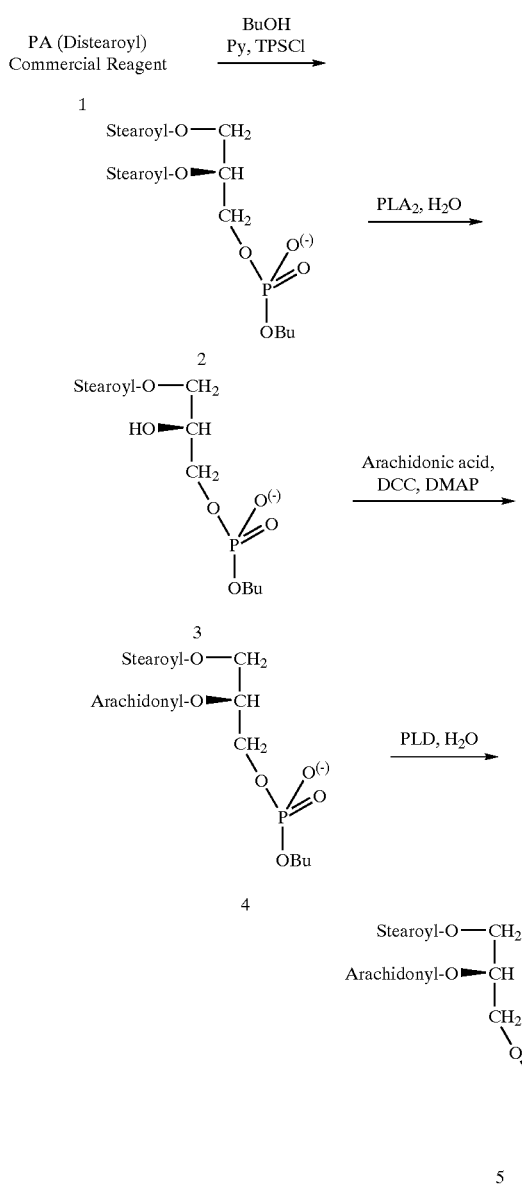

Ceramide-1-phosphoric acid derivatives are obtained from commercial sphingomyelins by the action of PLD; prior protection, for example by acetylation, of the 3-OH group is advantageous. Sphingosine-1-phosphoric acids protected at the amino as well as the 3-hydroxyl are prepared similarly from sphingosyl-phosphocholine.

Selectively Protected myo-inositol Synthons: Three pairs of enantiomerically pure O-protected optically resolved myo-inositol synthon, wherein the 1-equatorial hydroxyl is free, the 3-hydroxyl and at least three other hydroxyls carry O-protecting groups, were employed. These are prepared in greater than 99% purity, and the absolute configuration of each has been established unequivocally (Aneja and Parra, 1994; Aneja et al., 1995; Aneja et al. 1996).

2,3:5,6-O-Protected-myo-inositols: Representative key myo-inositols 1D-2,3:5,6-O-dicyclohexylidene-myo-inositol 3 (Scheme 3) and 1L-enantiomer 4 (not shown) were obtained from myo-inositol as described previously (Aneja et al., 1995); the corresponding 2,3:5,6-O-diisopropylidene derivatives were obtained similarly.

3,4,5,6-O-Protected-myo-inositols: Representative key myo-inositols 1D-3,4,5,6-O-tetrabenzyl-myo-inositol 7 (Scheme 4) and 1L-enantiomer 8 (not shown) were obtained from myo-inositol as described previously (Aneja and Parra, 1994).

2,3,4,5,6-O-Protected-myo-inositols: Representative key myo-inositols 1D-2,3,4,5,6-O-pentabenzyl-myo-inositol 16 and 1L-enantiomer (not shown) were obtained from myo-inositol as described previously (Aneja et al., 1994) or from 1D-1-O-allyl-2,3:5,6-O-dicyclohexylidene-myo-inositol 15 (and its 1L-1-O-allyl enantiomer) (Aneja et al. 1996) by the new method outlined in (Scheme 5)

Other myo-inositol synthons with the stipulated O-protection pattern may be employed. The temporary O-protecting groups are selected from those which can be introduced using inexpensive commercial reagents, and later easily removed; protecting groups compatible with unsaturated/polyunsaturated and related functional groups are preferred. Examples include but are not limited to 4-methoxy-benzyl, 3,4-dimethoxy-benzyl, tetrahydropyranyl, tetrahydro-furanyl, isopropylidene, 9-fluorenylmethyl, acetyl, levulinoyl, mono-, di- and tri-chloroacetyl, and methoxymethyl.

Condensation of Lipid and myo-Inositol Synthons: The condensation reaction between the lipid-phosphoric acid and the selectively O-protected myo-inositol is carried out in an aromatic or aliphatic tert. amine, using an arylsulfonyl chloride as the phosphoric acid activating reagent. Other activating chemistries and activating reagents, including carbodiimides such as dicyclohexylcarbodiimide, trichloroacetonitrile, and arylsulphonyl-triazoles, may be employed, or the phosphoric acid may be employed as its phosphoryl chloride or bromide derivative. Phosphorylation based on the phosphodiester condensation reaction between a lipid-phosphoric acid and an alcohol using pyridine as the tert. amine and 2,4,6-triisopropylbenzene-sulfonyl chloride (TPSCl) as the phosphoric acid activating reagent (Aneja et al., 1970) is preferred and this and related literature on phosphodiester synthesis is incorporated herein by reference.

The general protocol for phosphatidylation comprising reaction in anhydrous pyridine solution at r.t. between a phosphatidic acid activated by triisopropylbenzenesulfonyl chloride (TPSCl) was originally developed for primary alcohols (Aneja et al., 1970). Application of this protocol to 1D-2,3,4,5,6-penta-O-benzyl-myo-inositol gave less than 50% yield. Therefore, a new protocol was optimized for chiral secondary alcohols in the myo-inositol series. The molar ratios of the reactants, reaction temperature, and the order and rate of addition of phosphatidic acid to the other reactants were found to be critical parameters. Optimization of these parameters produced a dramatic, highly reproducible increase in yield. A typical optimized protocol is given in the section on synthesis from 1D-2,3,4,5,6-pentabenzyl myo-inositol. This novel protocol for condensation between lipid-phosphoric acids and the 1-O-(equatorial) hydroxyl of myo-inositol synthons, gives very high yields (upto 90%) of the (O-protected)-inositolphospholipid, and is an integral inventive step in the new approach to synthesis of inositol-phospholipid.

Deprotection: Protocols for removal of the protecting groups of (O-protected)-inositolphospholipid are discussed in connection with specific cases. Mild acid hydrolysis and transketalization of cyclohexylidene, tetrahydropyranyl and related ketal/hemiketals are suitable for most fattyacyl types including (poly)unsaturated lipids, and are preferred. Hydrogenolysis of benzyl group is best for saturated type lipids, but $BF_3$-EtSH is an effective special option.

Synthesis from sn-3-PA (1) and 1D-2,3:5,6-O-Dicyclohexylidene-myo-inositol (3); Reaction (Scheme 3) between the sn-3-PA 1 and 1D-2,3:5,6-O-dicyclohexylidene-myo-inositol 3 in anhydrous pyridine and activated by TPSCl at r.t. for 3 hr. using our general protocol for O-phosphatidylation (Aneja et al., 1969a, 1970), produced two products in ca. 70:30 ratio which were separated by flash chromatography on silica. The more polar (major) product was assigned the 1D-1-phosphatidyl structure 5, and the minor and less polar product the 1D-4-phosphatidyl-structure (not shown) based on $^1$H NMR data. Reaction of 5 in ethanol using p-toluene sulphonic acid (p-TSA) caused loss of the O-cyclohexylidene groups and gave 1D-1-(1-stearoyl-2-arachidonyl-sn-glycero-3-phospho)-myo-inositol 6.

Use of other sn-3-PAs, for instance dioleoyl-sn-3-PA in the above procedure gives the corresponding PtdIns products, and use of ceramide-phosphoric acid gives the sphingo-lipid analogue, 1D-1-(ceramide-phospho)-myo-inositol; the 1L-1- and the sn-glycero-1-phospho series diastereomers are obtained from the corresponding inositol and lipid synthons.

Scheme 3: Synthesis of 1D-1(1-stearoyl-2-arachidonyl-sn-glycero-3-phospho)-2, 3:5, 6-di-O-cyclohexylidine-myo-inositol (5), and 1D-1(1-stearoyl-2-arachidonyl-sn-glycero-3-phospho)-myo-inositol (6).

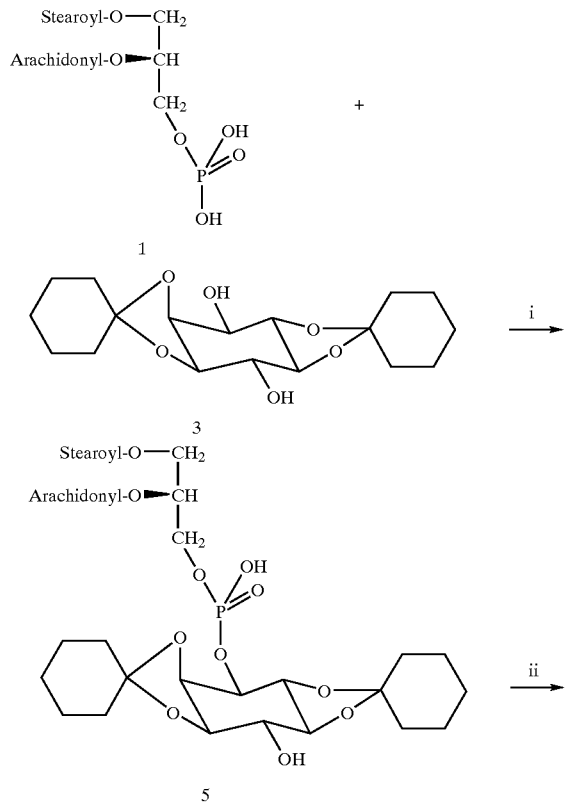

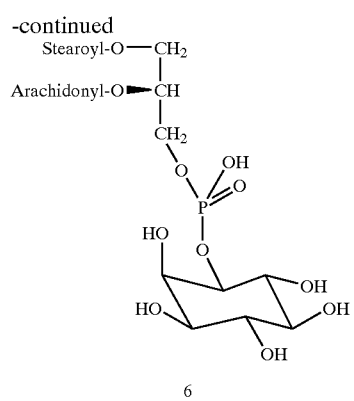

Total Synthesis from 3,4,5,6-tetra-O-protected-myo-inositols: The key myo-inositols 1D-3,4,5,6-tetra-O-benzyl-myo-inositol 7 and 1L-enatiomer 8 (not shown) were obtained from myo-inositol as described (systematic names 1L- and 1D-1,4,5,6-tetra-O-benzyl-myo-inositol respectively, Aneja and Parra, 1994). 3,4,5,6-Tetra-O-protected-myo-inositols synthons with protecting groups other than benzyl, for instance 4-methoxy-benzyl, were obtained similarly.

The chiral lipid synthons 1,2-difattyacyl-sn-glycero-3-phosphoric acids 9 (sn-3-PA) were prepared from the corresponding sn-phosphatidylcholines by lipolysis with phospholipase D (PLD) (Aneja, 1974).

Reaction (Scheme 4) between the 1D-3,4,5,6-tetra-O-benzyl-myo-inositol 7 in anhydrous pyridine and sn-3-PA 9 ($R^1CO=R^2CO$=fattyacyl) activated by TPSCl at r.t. for 3 hr. using our general protocol for O-phosphatidylation (Aneja et al., 1969a, 1970), produced two products in ca. 60:40 ratio (yield 45%) which were separated by flash chromatography on silica. The more polar (major) product was assigned the 1D-1-structure 10, and the minor and less polar product 1D-2-structure 11 based on $^1$H NMR data. Hydrogenolysis of 10 using Pd(OH)$_2$/C and H$_2$ at 45 psi produced 12, and of 11 gave 1D-2-PtdIns 13 (100% conversion, each) which is in fact the DL-2-(1,2-difattyacyl-sn-glycero-3-phospho)-myo-inositol because a plane of symmetry exists in unsubstituted and 2-substituted myo-inositols. Specifically, use of dioctanoyl-sn-3-PA 9 in the above procedure gave 12 and 13 ($R^1CO=R^2CO$=n-octanoyl).

Compound 12 ($R^1CO=R^2CO$=n-octanoyl) 1D-1-(1,2-Dioctanoyl-sn-glycero-3-phospho)-myo-inositol: $[\alpha]_D$+8.90 (c 0.45, CHCl$_3$—CH$_3$OH 4:1), ES(−) MS m/z 585.0 (M−H); $^1$H-NMR (400 MHz, CDCl$_3$—CD$_3$OD, 2:1) ppm 0.90 (t, 6H, CH$_3$), 1.29 (br s, 16H, (CH$_2$)$_8$), 1.61 (m, 4H, CH$_2$CH$_2$C=O), 2.29–2.36 (m, 4H,CH$_2$C=O), 3.30 (t, 1H, inositol 5-H), 3.46–3.48 (dd, 1H, inositol 3-H), 3.67(m, 1H, inositol 4-H), 3.80 (m, 1H, inositol 6-H), 3.92 (t, 1H, inositol 2-H), 4.05–4.17 (m, 2H, sn-3 CH$_2$), 4.45 (m, 2H, sn-1 CH$_2$), 4.28 (t, 1H, inositol 1H, inositol 1-H), 5.26 (m, 1H, sn-2 CH); $^{13}$C-NMR (100 MHz, CDCl$_3$—CD$_3$OD, 2:1) 173.69 & 173.35 (2 C=O), 76.24 (inositol C-1), 74.12 (inositol C-5), 72.10 (inositol C-4), 71.35 (inositol C-6), 71.19 & 70.98 (inositol C-2), 70.14 & 70.06 (sn-2 glycerol C), 63.46 (sn-3 glycerol C), 62.39 (sn-1 glycerol C), 33.82 (acyl chain sn-2 —CH$_2$), 33.68 (acyl chain sn-1 —CH$_2$), 31.29, 31.28, 24.51 & 24.45 ((CH$_2$)n), 22.19 (acyl chain —CH$_2$), 13.46 (acyl chain CH$_3$); $^{31}$P-NMR (162 MHz, CDCl$_3$—CD$_3$OD, 2:1) ppm (ext. H$_3$PO$_4$.) −0.259 (s).

Compound 13 ($R^1CO=R^2CO$=n-octanoyl), DL-2-(1,2-Dioctanoyl-sn-glycero-3-phospho)-myo-inositol: $[\alpha]_D$+7.25

(c 0.50, CHCl$_3$—CH$_3$OH 4:1), m/z 585.0 (M–H); $^1$H-NMR (400 MHz, CDCl$_3$—CD$_3$OD, 2:1) ppm 0.89 (t, 6H, CH$_3$), 1.29 (br s, 16H, (CH$_2$)$_8$), 1.61 (m, 4H, CH$_2$CH$_2$C=O), 2.33 (m, 4H,CH$_2$C=O), 3.28 (t, 1H, inositol 5-H), 3.52 (dT, 2H, inositol 1-H & 3-H), 3.63(m, 2H, inositol 4-H & 6-H), 4.17 (m, 1H, sn-1 CH$_2$), 4.22 (m, 2H, sn-3 CH$_2$), 4.40 (m, 1H, sn-1 CH$_2$), 4.68 (tD, 1H, inositol 2-H), 5.26 (m, 1H, sn-2 C H); $^{31}$P-NMR (162 MHz, CDCl$_3$—CD$_3$OD, 2:1) ppm (external H$_3$PO$_4$ ref.) –0.701 (s).

acid—water (80:20) at 100° C., evaporation to dryness, (ii) complete benzylation in DMF using NaH/BnBr and evaporation under 2 millitorr to remove all volatiles, and (iii) deallylation by successive heating with t-BuOK in DMSO followed by HOAc—H$_2$O (80:20), in a one pot procedure, gave (–)-2,3,4,5,6-penta-O-benzyl-myo-inositol 16 in 95% yield. The absolute configuration of 16 has been established unequivocally as 1D-2,3,4,5,6-penta-O-benzyl-myo-inositol (systematic name 1L-1,2,4,5,6-penta-O-benzyl-myo- Scheme 4: Synthesis of 1D-1-(1, 2-difattyacyl-sn-glycero-3-phospho)-myo-inositol (12) and DL-2-(1, 2-difattyacyl-sn-glycero-3-phospho)-myo-inositol (13) from 1D-3, 4, 5, 6-tetra-O-benzyl-myo-inositol (7) and sn-3-PA (9).

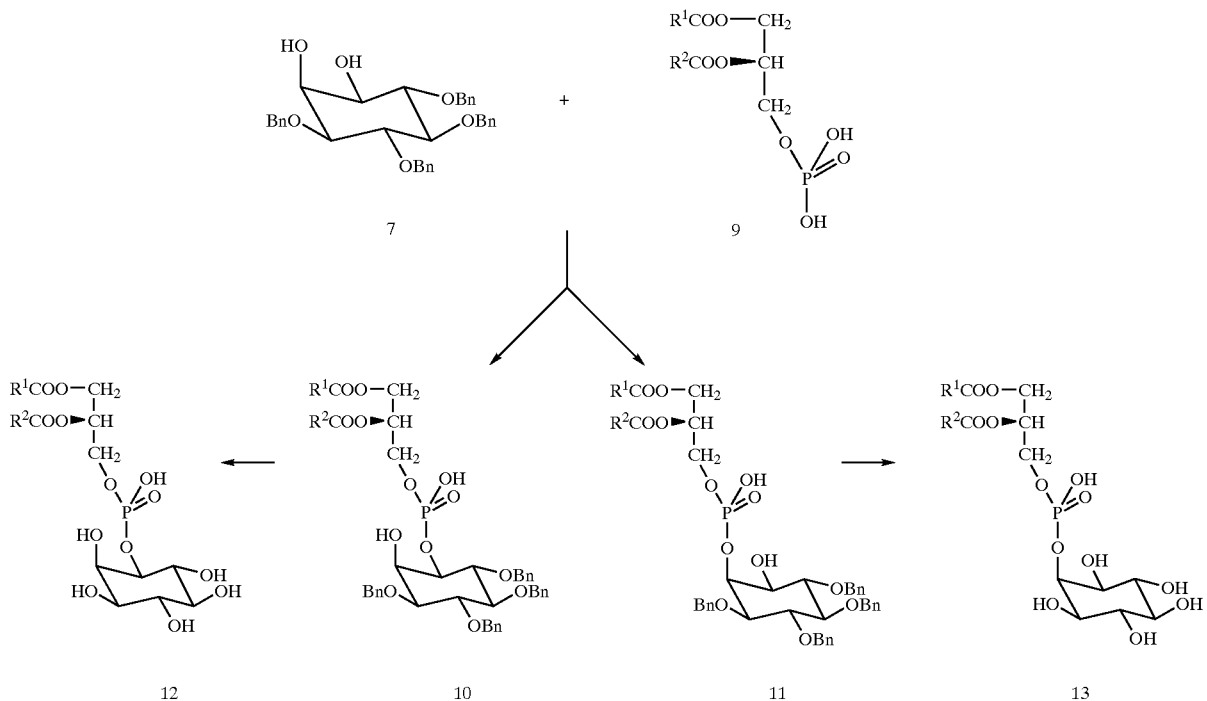

Reaction between 1L-3,4,5,6-tetra-O-benzyl-myo-inositol 8 (not shown) and dioctanoyl-sn-3-PA 9 (R$^1$CO=R$^2$CO=n-octanoyl) and deprotection gave 14, the 1L-myo-diastereomer of 12 (R$^1$CO=R$^2$CO=n-octanoyl) (structure not shown) and DL-2-PtdIns identical with 13 (R$^1$CO=R$^2$CO=n-octanoyl).

Compound 14 (structure not shown): 1L-1-(1,2-Dioctanoyl-sn-glycero-3-phospho)-myo-inositol: [α]$_D$+ 12.85 (c 0.50, CHCl$_3$—CH$_3$OH 4:1); m/z 585.0 (M–H); $^1$H—, $^{13}$C-NMR and $^{31}$P-NMR virtually identical with 1D-myo-diastereomer 12 (R$^1$CO=R$^2$CO=n-octanoyl). $^3$P-NMR varied somewhat with conditions. Notably, mixtures of 1D-myo-12 and 1L-myo-diastereomer 14 always showed a single sharp $^{31}$P-NMR peak.

PtdIns with other fattyacyls (heptanoyl, palmitoyl, stearoyl) were obtained from the corresponding sn-PAs 9.

Total Synthesis from 2,3,4,5,6-Penta-O-protected-myo-inositols: The starting material 1D-1-O-allyl-2,3:5,6-di-O-cyclohexylidene-myo-inositol 15 was obtained from myo-inositol in four steps as described (Aneja et al., 1996; Aneja, 2000). The reaction of 15 successively with (i) acetic inositol, Aneja et al., 1996). Analogues of 16 with other protecting groups, for instance 4-methoxy-benzyl, tetrahydropyranyl, tetrahydro-furanyl, and the respective 1L-1-enantiomers, were obtained similarly. The chiral lipid synthons 1,2-difattyacyl-sn-glycero-3-phosphoric acids 9 (sn-3-PA) were prepared from the corresponding sn-phosphatidylcholines by lipolysis with PLD (Aneja, 1974). The crucial esterification reaction of the secondary 1-hydroxyl group in 16 with the phosphoric acid in 9 gave less than 50% yield when phosphatidylation was conducted under conditions recommended for primary alcohols (Aneja et al., 1969a, 1970) but a dramatic, highly reproducible increase in yield to 90% was achieved by the following protocol. Typically, 0.15 mmole of sn-3-PA 9 was added gradually over one hr at 35–37° C. to a stirred solution of the alcohol 16 (0.1 mmole) and TPSCl (0.4 mmole) in anhydrous pyridine, and worked up by addition of water. The product 1D-1-(1,2-difattyacyl-sn-glycero-3-phospho)-2,3,4,5,6-penta-O-benzyl-myo-inositol 17 was purified by flash chromatography on silica, and debenzylated in t-BuOH with H$_2$ at 45 psi and Pd-C catalyst to produce a quantitative yield of the target 1D-1-(1,2-difattyacyl-sn-glycero-3-phospho)-myo-inositol 18.

Scheme 5: Synthesis of 1D-1-(1, 2-difattyacyl-sn-glycero-3-phospho)-myo-inositol (18) from 1D-2, 3, 4, 5, 6-penta-O-benzyl-myo-inositol (16) and sn-3-PA (9).

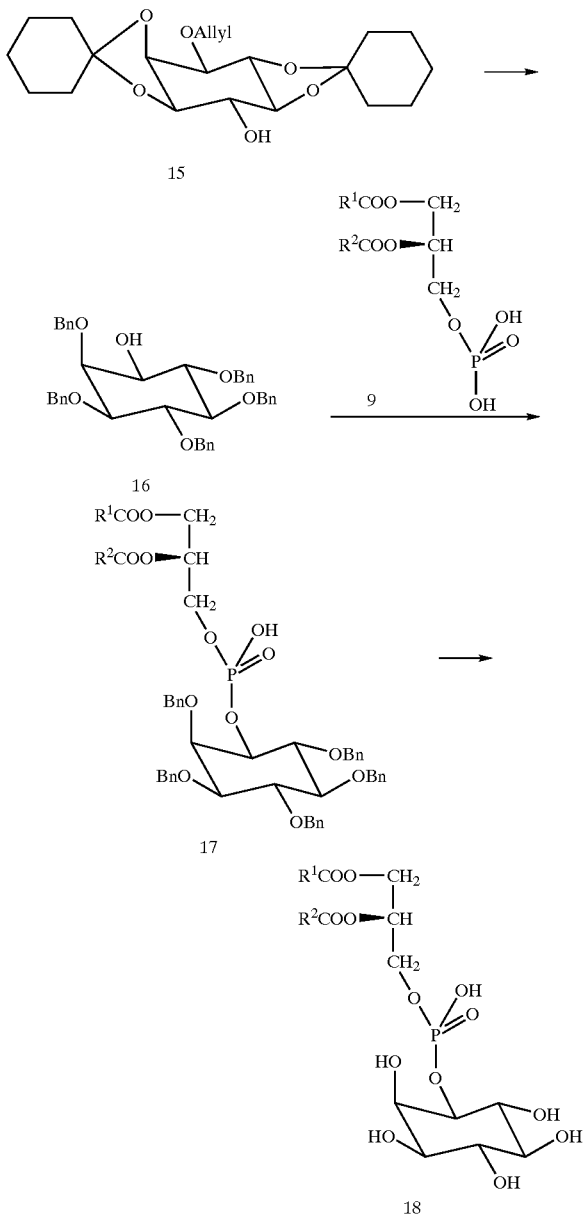

Synthesis as above using dioctanoyl sn-3-PA gave 1D-1-(1,2-dioctanoyl-sn-glycero-3-phospho)-myo-inositol 18 ($R^1CO=R^2CO$=n-octanoyl): $[\alpha]_D$+8.80 (c 0.45, CHCl$_3$—CH$_3$OH 4:1), ES(–) MS m/z 585.0 (M–H); $^1$H, $^{13}$C and $^{31}$P NMR identical with Compound 12 ($R^1CO=R^2CO$=n-octanoyl) prepared by Scheme 4. Synthesis using distearoyl sn-3-PA gave distearoyl PtdIns 18 ($R^1CO=R^2CO$=stearoyl), $[\alpha]_D$+5.67. PtdIns with other fattyacyls were prepared using the corresponding sn-3-PA 9 in Scheme 5. Synthesis starting with the 1L-enantiomer of 16 (Aneja et al., 1996) gave the 1L-1-series dioctanoyl PtdIns, [a]D+ 12.50 (c 0.40) m/z 585.0 (M–H); $^1$H, $^{13}$C and $^{31}$P NMR identical with compound 14 prepared from 1L-3,4,5,6-tetra-O-benzyl-myo-inositol.

Synthesis of Inositolphospholipids with Unsaturated Lipid Residues: Synthesis of various phosphatidyl-myo-inositols with unsaturated fattyacyls, ceramide-phospho-myo-inositols with unsaturation in the sphingo-lipid residue was illustrated (vide supra) using 2,3:5,6-O-protected-myo-inositol as the inositol synthon. Analogous syntheses are achieved using 3,4,5,6-tetra-O-protected-myo-inositol and 2,3,4,5,6-penta-O-protected-myo-inositol synthons wherein the protecting group is chosen from the group comprising but not limited to 4-methoxybenzyl, 9-fluorenylmethyl, tetrahydropyranyl, tetrahydrofuranyl, chioroacetyl, levulinoyl, and related moieties which do not require Pd metal catalyzed hydrogenolysis for deprotection. Thus, reaction between 1D-3,4,5,6-tetra-O-(4-methoxybenzyl)-myo-inositol and dioleoyl-sn-3-PA, and deprotection using moist DDQ yielded 1D-1(1,2-dioleoyl-sn-glycero-3-phospho)-myo-inositol as the inositolphospho lipid. Similarly, reaction using 1D-2,3,4,5,6-penta-O-tetrahydropyranyl-myo-inositol, and deprotection using acetic acid-water (80:20) at 65° C. gave 1D-1-(1,2-dioleoyl-sn-glycero-3-phospho)-myo-inositol.

Novel Inositolphospholipid molecular Species and Applications: The present methods have provided for the first time, novel pure individual molecular species of phosphatidyl-myo-inositols with unequivocal stereo-structures, carrying combinations of one saturated and one polyunsaturated fattyacyl, or a single polyunsaturated fattyacyl at both glycerol hydroxyls. The need for and non-availability of such PtdIns molecular species was highlighted earlier under "Related Art" and "Summary of the Invention." Preferred polyunsaturated fattyacyls include the diunsaturated octadecadienoate isomers linoleoyl, and conjugated-linoleoyl, octadecatrienoate isomers alpha- and gamma-linolenoyl, eicosanoyl, eicosenoyl, elcosadienoyl, eicosatrienoyl, arachidonyl, eicosapentaenoyl, and docosahexaenoyl, because the corresponding free fatty acids have favorable pharmnacodynamnic properties, including anticancer and antuinflammatory effects. Parinaric acid is fluorescent and provides a PtdIns which is well suited for highly sensitive analysis by fluorescence techniques. Preferred PtdIns include 1D-1-(1-stearoyl-2-arachidonyl-sn-glycero-3-phospho)-myo-inositol, 1D-1-(1-stearoyl-2-conjugated linoleoyl-sn-glycero-3-phospho)-myo-inositol, 1D-1-(1-stearoyl-2-eicosapenatenoyl-sn-glycero-3-phospho)-myo-inositol, and 1D-1-(1,2-di(conjugated linoleoyl)-sn-glycero-3-phospho)-myo-inositol. These novel PtdIns have utility as biochemical precursors of polyunsaturated fatty acids of the eicosanoid cycle, and diacylg-lycerol second messengers, formed respectively by the action of phospholipase $A_2$ and PtdIns-specific phospholipase C enzyme families. This is simulated in Example 1 by the action of phospholipase $A_2$ on 1D-1-(1-stearoyl-2-arachidonyl-sn-glycero-3-phospho)-myo-inositol which liberated arachidonic acid. 1D-1-(1-Stearoyl-2-arachidonyl-sn-glycero-3-phospho)-myo-inositol is the major species among numerous molecular species with different fattyacyls which occur in animal tissues derived PtdIns. For convenience, these are often referred to in biochemical literature as stearoyl-arachidonyl-PtdIns, and sometimes erroneously labeled as such in biochemical reagent catalogues. However, the pure molecular species 1D-1-(1-stearoyl-2-arachidonyl-sn-glycero-3-phospho)-myo-inositol has not been prepared previously. Novel analogues wherein the stearoyl residue in 1D-1-(1-stearoyl-2-arachidonyl-sn-glycero-3-phospho)-myo-inositol is replaced by an -amino-alkyl, -amino-alkanoyl or other -reactive group-alkyl residue and the arachidonyl is retained or replaced by other mono- or polyunsaturated fattyacyl, are useful intermediates for attaching reporter groups and for tethering to polymer and metal supports. Further, analogues in which a part or all of one or both alkyl chains are replaced by polyethylene glycol (PEG) residues are useful as water soluble congeners of inositolphospholipids. The aforementioned analogues are obtainable only by the present approach to synthesis. PtdIns encounter aqueous media in most applications and nature of the hydrates determine suitability, particularly ease of use in any application. These novel PtdIns hydrate readily to liquid crystalline phases, as exemplified in Example 9 for 1D-1-(1-stearoyl-2-arachidonyl-sn-glycero-3-phospho)-myo-inositol, and thus have advantages over long straight chain saturated PtdIns which are comparatively difficult to hydrate and often form intractable hydrates. The structural types of the liquid crystalline phases are established by X-ray crystallographic analysis of the hydrated lipids. Finally, the high purity PtdIns molecular species are analytical reference standards for anaylsis of natural PtdIns in tissues and cells by various mass spectral modes, especially inotrap electrospray for quantitation. In this application, the 1-stearoyl-2-eicosdienoyl- and 1-stearoyl-2-eicosatrienoyl type PtdIns are found to be extremely valuable as internal references for quantitation of cellular and tissue as their molecular masses differ by 4 and 2 units from 1-stearoyl-2-arachidonyl-PtdIns which is the single most abundant molecular species in cells.

New Criteria for Structural and Steoreochemical Configuration of PtdIns

Synthesis by the new approach, particularly Scheme 5, provided authentic reference samples of pure diastereomers of PtdIns. The structures and absolute stereochemistry of these PtdIns follow directly from the synthetic methods and the known absolute configurations of sn-3-phosphatidic acids and O-protected-myo-inositol synthons, and were supported by $^1H$, $^{13}C$ and $^{31}P$ NMR spectra. As anticipated, $^1H$-NMR of DL-2-PtdIns show tD signal at ä 4.66, 4.68 ($J_{HCCH,cis}$ 2.44 & 2.1; $J_{HCOP}$ 8.24) which is characteristic of the 2-H in a 2-phospho-myo-inositol, the 1-H & 3-H, and 4-H & 6-H resonances show overlapping two proton signals, and can be distinguished from the 1D-1- (or 1L-1-) PtdIns. $^{31}P$-NMR of DL-2- and 1D-1-mixtures show single peaks for each ingredient. Further, the structurally isomeric 1- and 2-PtdIns were separated by TLC on boric acid impregnated silica plates. Thus contamination of 1D-1- (or 1L-1-) PtdIns with DL-2-PtdIns can be detected and measured easily by the multifarious criteria established in the present invention. None was found in synthetic 1D-1-PtdIns prepared according to the present invention.

Authentic reference samples of 1D-1- and 1L-1-PtdIns prepared by methods of the present invention could not be separated by chromatography, and their $^1H$, $^{13}C$, and $^{31}P$ NMR spectra showed no significant differences. Critically, the $^{31}P$ NMR spectrum of a mixture of 1D-1- and 1L-1-PtdIns showed a single peak. Thus, optical rotation emerges as the cardinal stereochemically significant parameter for diastereomer characterization.

The various PtdIns differ in fattyacyl type and hence molecular weight. To normalize for these differences in the homologous series, we have proposed comparison of molar rotations [φ] using the value+51 obtained for natural PtdIns as the bench mark for 1D-1-(sn-3-phosphatidyl)-myo-inositol absolute configuration (Aneja and Aneja, 2000). [φ] values for our authentic 1D-1-dioctanoyl PtdIns and 1D-1-distearoyl PtdIns are+51.57 and+51.70 respectively. These values are identical with the bench mark and thus confirm the 1D-1-(sn-3-phosphatidyl)-myo-inositol absolute configuration. The molar rotation values calculated from the published $[\alpha]_D$ for 1D-1-PtdIns are significantly larger than+ 51, and suggest contamination with 1L-1-series PtdIns. Contrary to recent publications which reported negative sign of rotation for 1L-1-series PtdIns (Garigapati and Roberts, 1993), the reference 1L-1-series PtdIns prepared herein all showed a positive sign of optical rotation with [φ]+74.13. Therefore, [φ]+74 is offered as the bench mark for 1L-1-(sn-3-phosphatidyl)-myo-inositol series. This suggests that the much higher specific and thereby the molar rotation of the prior art preparations of 1D-1-(sn-3-phosphatidyl)-PtdIns are due to contamination with 1L-1-(sn-3-phosphatidyl)-PtdIns diastereomers. In contrast, the PtdIns products of the synthesis, characterized by molar rotation equal to the bench-mark values are pure individual diastereomers, and represent uniquely pure preparations of PtdIns.

EXAMPLES

General Procedures

Reactions were carried out mostly on 0.1 milli-molar scale except where noted otherwise. The progress of reactions was monitored by thin layer chromatography (TLC) on silicagel G plates. Final products were judged to be >99% pure by TLC. Satisfactory MS (ES, MALDI-TOF) and $^1H$ NMR (400 MHz) data conforming to the assigned structure were obtained for all new compounds.

1D-2,3:5,6-O-dicyclohexylidene-myo-inositol (systematic name 1L-1,2:4,5-O-dicyclohexylidene-myo-inositol) and 1L-2,3:5,6-O-dicyclohexylidene-myo-inositol (systematic name 1D-1,2:4,5-O-dicyclohexylidene-myo-inositol) are prepared from myo-inositols as described (Aneja et al., 1994). 1D-1,2,4,5,6-penta-O-benzyl-myo-inositol (common name 1L-2,3,4,5,6-penta-O-benzyl-myo-inositol) and 1L-1,2,4,5,6-penta-O-benzyl-myo-inositol (common name 1D-2,3,4,5,6-penta-O-benzyl-myo-inositol) are prepared from 1D- and 1L-3-O-allyl-1,2:4,5-di-O-cyclohexylidene-myo-inositols as described (Aneja and Parra, 1994). 1D-1,4,5,6-tetra-O-benzyl-myo-inositol (common name 1L-3,4,5,6-tetra-O-benzyl-myo-inositol) and 1L-1,4,5,6-tetra-O-benzyl-myo-inositol (common name 1D-3,4,5,6-tetra-O-benzyl-myo-inositol) are prepared as described (Aneja et al., 1994). All were obtained in >99% enantiomeric purity. Lipid synthons were prepared as described in earlier sections.

Example 1

1D-1-(1-Stearoyl-2-arachidonyl-sn-glycero-3-phospho)-myo-inositol. 1D-2,3:5,6-O-dicyclohexylidene-myo-inositol, 1-O-stearoyl-2-O-arachidonyl-sn-glycero-3-phosphoric acid (1.5 equiv.) in anhydrous pyridine at 22° C., was treated with TPSCl (3 equiv.). After 2 hr the reaction was allowed to warm to r.t. and treated with water (1.2 equiv.), and evaporated to near dryness in a vacuum, treated with cold water (3 equiv.) and again evaporated to dryness. The crude product so obtained was purified by chromatography on silica eluted with a gradient of $CHCl_3$—$CH_3OH$—$NH_4OH$, gave the more polar of two as the main product, 1D-1-(1-stearoyl-2-arachidonyl-sn-glycero-3-phospho)-2,3:5,6-O-dicyclohexylidene-myo-inositol, yield 45%. The latter was heated in t-BuOH, water and p-TSA at 70° C., and the deprotected product purified by chromatography on silica $^1H$ NMR showed aromatic peaks for residual p-TSA. Deprotection was next effected by heating in ethanol using Nafion, a polymeric sulphonic acid, as catalyst. Chromatography gave pure 1D-1-(1-Stearoyl-2-arachidonyl-sn-glycero-3-phospho)-myo-inositol (StArach-PtdIns), yield 76%, −m/z 885.6 (M−H)−; $^{31}$P d 0.422 ppm; $[\alpha]_D$+5.48 (c 0.40, $CHCl_3$—$CH_3OH$ 4:1); fattyacyls by GC of methyl esters from methanolysis, and $PLA_2$: 1,2-fattyacyls: 18:0 51.9%, 20:4 49.05%; 2-fattyacyls: 18:0 4.1%, 20:4 95.7% (see below).

Lipolysis of 1D-1-(1-Stearoyl-2-arachidonyl-sn-glycero-3-phospho)-myo-inositol Catalyzed by Phospholipase $A_2$: A dispersion of 1D-1-(1-Stearoyl-2-arachidonyl-sn-glycero-3-phospho)-myo-inositol (11 mg) in 0.4 ml of 0.025 M $Na_2B_4O_7$ buffer containing 0.72 mM $CaCl_2$, prepared as above, diethyl ether (2 ml) and phospholipase $A_2$ (from Crotalus adamanteous, 0.2 mg in 0.1 ml buffer) was stirred at 30–31° C. for 6 hr. The mixture was acidified (pH 3) with 0.02 M HCl, the lipids extracted into $CHCl_3$, and treated with diazomethane solution to convert free fatty acids into methyl esters. The methyl ester fraction was isolated by chromatography over silica in a micropipette eluted with hexane-ether (9:1) and subjected to GC analysis using an HP-225 0.25 mm diam×30 m film capillary column at 180–220° C. Composition of the fatty acid methyl esters: stearate 4.1%, arachidonate 95.7% represents the 2-fattyacyl composition. The total fattyacyl determined by GC of methyl esters from acid-catalyzed methanolysis, representing both the 1- and 2-fattyacyls was: stearate 51.9%, arachidonate 49.05%.

Example 2

1D-1-(1,2-Dioctanoyl-sn-glycero-3-phospho)-2,3,4,5,6-penta-O-benzyl-myo-inositol. A solution of 1,2-dioctanoyl-sn-glycero-3-phosphoric acid and 1D-2,3,4,5,6-penta-O-benzyl-myo-inositol (systematic name 1L-1,2,4,5,6-penta-O-benzyl-myo-inositol) in anhydrous pyridine at r.t. was treated with triisopropylbenzene sulphonyl chloride (TPSCl) (molar ratios 2:1:4). After 3 hr., water (excess) was added, the mixture evaporated to dryness in a vacuum and the residue extracted with ether. The ether soluble fraction was purified by chromatography on silicagel eluted with a gradient of $CHCl_3$—$CH_3OH$—$NH_4OH$, gave 1D-1-(1,2-dioctanoyl-sn-glycero-3-phospho)-2,3,4,5,6-penta-O-benzyl-myo-inositol, yield 78%, +m/z 1037.4 (M+H), $[\alpha]_D$+13.13 (c 0.8, $CHCl_3$).

Example 3

1L-1-(1,2-Dioctanoyl-sn-glycero-3-phospho)-2,3,4,5,6-penta-O-benzyl-myo-inositol. This was prepared from 1L-2,3,4,5,6-penta-O-benzyl-myo-inositol (systematic name 1D-1,2,4,5,6-penta-O-benzyl-myo-inositol) exactly as described above for 1D-1-(1,2-dioctanoyl-sn-glycero-3-phospho)-2,3,4,5,6-penta-O-benzyl-myo-inositol. Yield 81%, +m/z 1037.4 (M+H), $[\alpha]_D$−7.023 (c 0.8, $CHCl_3$).

Example 4

1D-1-(1,2-Dioctanoyl-sn-glycero-3-phospho)-myo-inositol. 1D-1-(1,2-dioctanoyl-sn-glycero-3-phospho)-2,3,4,5,6-penta-O-benzyl-myo-inositol and Pd-black (catalyst) in tert-butanol at room temperature was shaken in $H_2$ gas at 50 psi for 36 hr. The catalyst was removed by filtration, and the filtrate evaporated to dryness in a vacuum. The residue was pure D-1-(1,2-dioctanoyl-sn-glycero-3-phospho)-myo-inositol, yield 100%; $[\alpha]_D$+8.90 (c 0.45, $CHCl_3$—$CH_3OH$ 4:1); ES(−) MS m/z 585.0 (M−H)−; $^1$H-NMR (400 MHz, $CDCl_3$—$CD_3OD$, 2:1) d ppm 0.90 (t, 6H, $CH_3$), 1.29 (br s, 16H, $(CH_2)_8$), 1.61 (m, 4H, $CH_2CH_2C$=O), 2.29–2.36 )(m, 4H,$CH_2C$=O), 3.30 (t, 1H, inositol 5-H), 3.46–3.48 (dd, 1H, inositol 3-H), 3.67(m, 1H, inositol 4-H), 3.80 (m, 1H, inositol 6-H), 3.92 (t, 1H, inositol 2-H), 4.05–4.17 (m, 2H, sn-3 $CH_2$), 4.45 (m, 2H, sn-1 $CH_2$), 4.28 (t, 1H, inositol 1-H), 5.26 (m, 1H, sn-2 $CH$); $^{13}$C-NMR (100 MHz, $CDCl_3$—$CD_3OD$, 2:1) 173.69 & 173.35 (2 C=O), 76.24 (inositol C-1), 74.12 (inositol C-5), 72.10 (inositol C-4), 71.35 (inositol C-6), 71.19 & 70.98 (inositol C-2), 70.14 & 70.06 (sn-2 glycerol C), 63.46 (sn-3 glycerol C), 62.39 (sn-1 glycerol C), 33.82 (acyl chain sn-2 a-$CH_2$), 33.68 (acyl chain sn-1 a-$CH_2$), 31.29, 31.28, 24.51 & 24.45 (($CH_2)_n$), 22.19 (acyl chain w-$CH_2$), 13.46 (acyl chain $CH_3$); $^{31}$P-NMR (162 MHz, $CDCl_3$—$CD_3OD$, 2:1) d ppm (ext. $H_3PO_4$.) −0.259 (s).

Example 5

1L-1-(1,2-Dioctanoyl-sn-glycero-3-phospho)-myo-inositol. Hydrogenolysis of 1L-1-(1,2-dioctanoyl-sn-glycero-3-phospho)-2,3,4,5,6-penta-O-benzyl-myo-inositol as described above for the 1D-1-analogue gave 1L-1-(1,2-dioctanoyl-sn-glycero-3-phospho)-myo-inositol, yield 100%, −m/z 585.0 (M−H), $[\alpha]_D$+12.3 (c 0.9, $CHCl_3$—$CH_3OH$ 9:1); $^1$H—, $^{13}$C-NMR and $^{31}$P-NMR virtually identical with 1D-myo-diastereomer (Example 4); d $^{31}$P-NMR varied somewhat with conditions. Notably, mixtures of 1D-myo- and 1L-myo-diastereomer always showed a single sharp $^{31}$P-NMR peak.

Example 6

DL-2-(1,2-Dioctanoyl-sn-glycero-3-phospho)-3,4,5,6-tetra-O-benzyl-myo-inositol. A solution of 1,2-dioctanoyl-sn-glycero-3-phosphoric acid and 1D-3,4,5,6-tetra-O-benzyl-myo-inositol (systematic name 1L-1,4,5,6-tetra-O-benzyl-myo-inositol) in anhydrous pyridine at r.t. was treated with triisopropylbenzene sulphonyl chloride (TPSCl) (molar ratios 1: 1:2). After 3 hr., water (excess) was added, the mixture evaporated to dryness in a vacuum and the residue extracted with ether. The ether soluble fraction was purified by chromatography on silicagel eluted with a gradient of $CHCl_3$—$CH_3OH$—$NH_4OH$, gave 1D-1-(1,2-dioctanoyl-sn-glycero-3-phospho)-3,4,5,6-tetra-O-benzyl-myo-inositol, yield 48%, −m/z 945.2 (M−H), $[\alpha]_D$−2.15 (c 1.4, $CHCl_3$), followed by DL-2-(1,2-dioctanoyl-sn-glycero-3-phospho)-3,4,5,6-tetra-O-benzyl-myo-inositol, yield 38%, −m/z 945.2 (M−H), $[a]_D$+18.64 (c 0.8, $CHCl_3$).

Example 7

DL-2-(1,2-Dioctanoyl-sn-glycero-3-phospho)-myo-inositol. DL-2-(1,2-dioctanoyl-sn-glycero-3-phospho)-3,4,5,6-tetra-O-benzyl-myo-inositol and Pd-black (catalyst) in tert-butanol at room temperature was shaken in $H_2$ gas at 50 psi for 36 hr. The catalyst was removed by filtration, and the filtrate evaporated to dryness in a vacuum. The residue was pure DL-2-(1,2-dioctanoyl-sn-glycero-3-phospho)-myo-inositol, yield 100%; $[\alpha]_D$+7.25 (c 0.50, $CHCl_3$—$CH_3OH$ 4:1), −m/z 585.0 (M−H)−; $^1$H-NMR (400 MHz, $CDCl_3$—$CD_3OD$, 2:1) d ppm 0.89 (t, 6H, $CH_3$), 1.29 (br s, 16H, $(CH_2)_8$), 1.61 (m, 4H, $CH_2CH_2C$=O), 2.33 (m, 4H, C$H_2C$=O), 3.28 (t, 1H, inositol 5-H), 3.52 (dT, 2H, inositol 1-H & 3-H), 3.63(m, 2H, inositol 4-H & 6-H), 4.17 (m, 1H, sn-1 $CH_2$), 4.22 (m, 2H, sn-3 $CH_2$), 4.40 (m, 1H, sn-1 $CH_2$), 4.68 (tD, 1H, inositol 2-H), 5.26 (m, 1H, sn-2 $CH$); $^{31}$P-NMR (162 MHz, $CDCl_3$—$CD_3OD$, 2:1) d ppm (external $H_3PO_4$ ref.) −0.701 (s).

Example 8

1D-1-(1,2-Distearoyl-sn-glycero-3-phospho)-myo-inositol. Hydrogenolysis of 1D-1-(1,2-distearoyl-snglycero-3-phospho)-2,3,4,5,6-penta-O-benzyl-myo-inositol as described above for the dioctanoyl series gave 1D-1-(1,2-distearoyl-sn-glycero-3-phospho)-myo-inositol, yield 100%, −m/z 865.6 (M−H), [α]$_D$+5.9 (c 0.2, CHCl$_3$—CH$_3$OH 9:1).

Example 9

Hydration Behavior of 1,2-Disaturated-fattyacyl and 1-Saturated-fattyacyl-2-Polyunsaturated-fattyacyl type PtdIns. The mesogenic behavior of 1D-1-(1-stearoyl-2-arachidonyl-sn-glycero-3-phospho)-myo-inositol versus 1D-1-(1,2-distearoyl-sn-glycero-3-phospho)-myo-inositol was compared. A solution of each lipid (5 mg) in CHCl$_3$ was evaporated to obtain a thin film in a small test tube. The residue was left under a high vacuum for 12 hr to remove traces of solvent. Pure water (0.2 ml, HPLC grade) was added, the tube contents mixed by agitation over a vortex mixer and in bath type sonicator under Argon gas at 35–36° C. The resulting dispersion was examined on a microscope slide under crossed polarizers in a microscope (Small, 1986). Sample prepared with 1D-1-(1-stearoyl-2-arachidonyl-sn-glycero-3-phospho)-myo-inositol appeared as a clear fluid birefringent phase similar to the myelin figures formed by egg yolk phosphatidylcholine. Sample prepared with 1D-1-(1,2-distearoyl-sn-glycero-3-phospho)-myo-inositol showed undispersed powder-like material.

All of the compositions and methods disclosed and claimed herein can be made and executed by those of ordinary skill in the art without undue experimentation in light of the present disclosure. While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the claimed invention. More specifically, it will be apparent to those of ordinary skill in the art that certain agents that are chemically, structurally, functionally and/or physiologically related may be substituted for the particular agents described herein in order to yield the same, similar or otherwise beneficial results in accordance with the invention. All such similar substitutes and modifications apparent to those skilled in the art are to be included within the spirit, scope and concept of the invention as defined by the appended claims.

REFERENCES

The following references, to the extent that they provide exemplary procedural or other details supplementary to those set forth herein, are specifically incorporated herein by reference.

Aneja, R.; Chadha, J. S.; Davies, A. P. 1970, Biochim. Biophys. Acta, 218, 102–111.
Aneja, R.; Chadha, J. S.; Yoell, R. W. 1971, Fette Seifen Anstrichmittel, 73, 643.
Aneja, R. 1974, Biochem. Soc. Trans., 2, 38.
Aneja, R.; Parra, A.; Elbaggari, A. National Organic Symposium, A. C. S. Ithaca, N.Y., Jun. 18–22, 1989.
Aneja, R. and Parra, A. 1994, Tetrahedron Lett., 35, 525–526.
Aneja, R.; Aneja, S.; Pathak, V. P.; Ivanova, P. T. 1994, Tetrahedron Lett. 35, 6061–6062.
Aneja, R.; Aneja, S. G.; Parra, A. 1995, Tetrahedron Asymmetry, 6,17–18.
Aneja, R.; Aneja, S. G.; Parra, A. 1996, Tetrahedron Lett. 37, 5081–5082.
Aneja, R. and Aneja, S. G. 1999 In Advances in Phosphoinositides. Ed. K. S. Bruzik, ACS Symposium Series 718 Washington D.C. 222–231.
Aneja, R. and Aneja, S. 2000, Tetrahedron Lett. 41, 847–850.
Bell, R. M.; Exton, J. H.; Prescott, S. M. (Eds.) Lipid Second Messengers—Handbook of Lipid Research; Plenum Press: New York, N.Y. 1996, Vol 8.
Berridge M. J. 1984, Biochem. J., 220, 345.
Berridge M. J. 1987, Annu. Rev. Biochem., 56, 59.
Berridge, M. J. 1993, Nature, 361, 315.
Billington, D. C. 1993, The Inositol Phosphates, VCH Publishers, New York. 30.
Carter, H. E.; Johnson, P.; Weber, E. J. 1965, Annu. Rev. Biochem., 34, 109.
Colacicco, G. and Rapport, M. M. 1967, J. Lipid Res., 8, 513.
Duckworth, B. C. and Cantley, L. C. Lipid Second Messengers—Handbook of Lipid Research; Plenum Press: New York, N.Y. 1996, Vol 8, 125–175.
Englund, P.T. 1993, Annu. Rev. Biochem., 62, 121.
Ferguson, M. A. J. and Williams, A. F. 1988, Annu. Rev. Biochem., 57, 285.
Garigapati, V. R. and Roberts, M. F. 1993, Tetrahedron Lett., 34, 769–772.
Gigg, R. 1980, Chem. Phys. Lipids, 26, 287.
Hokin, L. E. 1985, Ann. Rev. Biochem., 54, 204.
Jett M.; Chudzik, J.; Alviing, C.R.; Stanacev, N. Z. 1985, Cancer Res., 45, 4810.
Jett-Tilton, M. 1991, U.S. Pat. No. 4,997,761 (to Houston Biotechnology, Inc.).
Jones M.; Rana, K. K.; Ward, J. G. 1989, Tetrahedron Lett., 30, 5353.
Kozikowski, A. P.; Faug, A. H.; Powis, G. 1993, U.S. Pat. No. 5,227,508. (to Mayo Foundation, Rochester, Minn.).
Lapetina, E. G.; Billah, M. M.; Cuatrecasas, P. 1981, Nature, 292, 367.
Lee, K. D.; Hong, K.; Papahadjopoulos, D. 1992, Biochim. Biophys. Acta, 1103, 185.
Leung, L. W.; Lin, W. Y.; Richard, C.; Bittrnan, R.; Arthur, G. 1998a, J. Liposome Res., 8, 213.
Leung, L. W.; Vilcheze, C.; Bittman, R. 1998b, Tetrahedron Lett., 39, 2921.
Lyutik, A. I.; Sukhanov, V. I.; Shvets, V. I.; Evstigneeva, R. P. 1974, Zh. Obshch. Khim. 44, 2595.
Mandal, S. B.; Sen, P. C.; Chakrabarti, P. 1980, Phytochemistry, 19, 1661.
Mandala, S. M.; Thornton, R. A.; Milligan, J.; Rosenbach, M.; Garciacalvo, M.; Bull, H. G.; Harries, G.; Abruzzo, G. K.; Flattery, A. M.; Gill, C. J.; Bartizal, K.; Dreikom, S.; Kurtz, M. B. 1998, J. Biol. Chem., 273, 14942.
Molotkovsky, J. G. and Bergelson, L. D. 1973, Chem. Phys. Lipids, 11, 135.
Neises, B. and Steglich, W. 1978, Angew. Chem. Int. Ed. Engl., 17, 522.
Nishizuka, Y. 1986, Science, 233, 305.
Rebecchi, M. J. R.; Eberhardt, T.; Delaney, S. A.; Bittman, R. 1993, J. Biol Chem., 268, 1735.
Rhee, S. G.; Suh, P. G.; Ryu, S. H.: Lee, S. Y. 1989, Science, 244, 546.
Salamonczyk, G. M. and Bruzik, K. S. 1990, Tetrahedron Lett., 31, 2015.
Saltiel, A. R.; Fox, J. A.; Sherline, P.; Cuatrecasas, P. 1986, Science, 233, 967.
Shvets, V. I.; Klyashchitskii, B. A.; Stepanov, A. E.; Evstigneeva, R. P. 1973, Tetrahedron, 29, 331.
Small, D. M. The Physical Chemistry of Lipids—Handbook of Lipid Research; Plenum Press: New York, N.Y. 1986, Vol 4, 475.

Somerharju, P. J.; Virtanen, J. A.; Eklund, K. K.; Vainio, P.; Kinnunen, P. 1985, *Biochemistry*, 24, 2773.

Toker, A.; Meyer, M.; Reddy, K.; Falck, J. R.; Aneja, R.; Aneja, S.; Parra, A.; Burns, D. J.; Cantley, L. M. 1994, *J. Biol. Chem.*, 269, 32358.

Ward, J. G.; Young, R. C. 1988, *Tetrahedron Lett.*, 29, 6013.

Whitman, M.; Downes, C. P.; Keeler, M.; Keller, T.; Cantley, L. 1988, *Nature*, 332, 644.

Yang, S. S.; Beattie, T. R.; Durette, P. L.; Gallagher, T. F.; Shen, T. Y. 1985, U.S. Pat. No. 4,515, 722 (to Merck & Co. Inc.).

Young, R. C.; Downes, C. P.; Eggleston, D. S.; Jones, M.; Macphee, C. H.; Rana, K. K.; Ward, J. G. 1990, *J. Med. Chem.* 33, 641.

What is claimed is:

1. A process for synthesizing a substantially single diastereomeric form of an inositolphospholipid, wherein said inositolphospholipid has the target phosphatidyl-myo-inositol structure:

1D-1-(1-fattyacyl$^1$-2-fattyacyl$^2$-sn-glycero-3-phospho)-myo-inositol;

1D-1-(3-fattyacyl$^1$-2-fattyacyl$^2$-sn-glycero-1-phospho)-myo-inositol;

1L-1-(1-fattyacyl$^1$-2-fattyacyl$^2$-sn-glycero-1-phospho)-myo-inositol;

1L-1-(3-fattyacyl$^1$-2-fattyacyl$^2$-sn-glycero-1-phospho)-myo-inositol;

wherein fattyacyl$^1$ and fattyacyl$^2$ are identical or non-identical;

said process comprising the steps of:

(a) obtaining a lipid synthon, wherein said lipid synthon is a substantially pure enantiomeric form of 1-fattyacyl$^1$-2-fattyacyl$^2$-sn-glycero-3-phosphoric acid or 3-fattyacyl$^1$-2-fattyacyl$^2$-sn-glycero-1-phosphoric acid;

(b) obtaining a myo-inositol synthon, wherein said myo-inositol synthon is a substantially pure enantiomeric form of a selectively partially O-protected 1D-1-myo-inositol, wherein at least the 1-equatorial hydroxyl is free, the 3-hydroxyl and at least three other hydroxyls carry temporary O-protecting groups;

(c) reacting said lipid synthon with said myo-inositol synthon in the presence of a phosphoric group activating reagent system, thereby linking the two synthons by a phosphodiester bond and creating an O-protected derivative of the target phosphatidyl-myo-inositol as an intermediate; and (d) subjecting said O-protected intermediate to a deprotection process to completely remove the protecting groups, thereby forming the target phosphatidyl-myo-inositol diastereomer.

2. The process of claim 1, further comprising subjecting said target phosphatidyl-myo-inositol diastereomer to purification to eliminate non-phosphatidyl-myo-inositol contaminants.

3. The process of claim 1, wherein said inositolphospholipid has the target phosphatidyl-myo-inositol structure 1D-1-(1-fattyacyl$^1$-2-fattyacyl$^2$-sn-glycero-3-phospho)-myo-inositol or 1D-1-(3-fattyacyl$^1$-2-fattyacyl$^2$-sn-glycero-1-phospho)-myo-inositol.

4. The process of claim 1, wherein said inositolphospholipid has the target phosphatidyl-myo-inositol structure 1L-1-(1-fattyacyl$^1$-2-fattyacyl$^2$-sn-glycero-3-phospho)-myo-inositol or 1L-1-(3-fattyacyl$^1$-2-fattyacyl$^2$-sn-glycero-1-phospho)-myo-inositol.

5. The process of claim 1, where said target phosphatidyl-myo-inositol comprises a saturated chain lipid.

6. The process of claim 1, where said target phosphatidyl-myo-inositol comprises a lipid chain comprising a functional group with at least one double or triple bond.

7. A substantially single diastereomeric form of an inositolphospholipid prepared by the process of claim 1.

8. A substantially single diastereomeric form of an inositolphospholipid, wherein said inositolphospholipid has the phosphatidyl-myo-inositol structure:

1D-1-(1-fattyacyl$^1$-2-fattyacyl$^2$-sn-glycero-3-phospho)-myo-inositol;

1D-1-(3-fattyacyl$^1$-2-fattyacyl$^2$-sn-glycero-1-phospho)-myo-inositol;

1L-1-(1-fattyacyl$^1$-2-fattyacyl$^2$-sn-glycero-3-phospho)-myo-inositol;

1L-1-(3-fattyacyl$^1$-2-fattyacyl$^2$-sn-glycero-1-phospho)-myo-inositol;

wherein fattyacyl$^1$ and fattyacyl$^2$ are identical or non-identical; and said inositolphospholipid has a molar rotation substantially equal to the bench-mark value established for the specific diastereomer structure.

\* \* \* \* \*

UNITED STATES PATENT AND TRADEMARK OFFICE
CERTIFICATE OF CORRECTION

PATENT NO. : 6,737,536 B1
DATED : May 18, 2004
INVENTOR(S) : Rajindra Aneja

It is certified that error appears in the above-identified patent and that said Letters Patent is hereby corrected as shown below:

Column 23,
Line 25, delete "glycero-1", and insert -- glycero-3 -- therefor.

Column 23, line 20 through column 24, line 6, delete "myo", all occurences and insert --*myo* -- at each instance.

Column 23, line 20 through column 24, line 6, delete "sn", all occurences and insert -- *sn* -- at each instance.

Column 23, line 20 through column 24, line 6, delete "O", all occurences And insert -- *O* -- at each instance.

Column 24,
Lines 7-10, delete "myo", all occurences and insert -- *myo* -- at each instance.
Lines 11-15, delete "myo", all occurences and insert -- *myo* -- at each instance.
Lines 11-15, delete "sn", all occurences and insert -- *sn* -- at each instance.
Lines 16-20, delete "myo", all occurences and insert -- *myo* -- at each instance.
Lines 16-20, delete "sn", all occurences and inert -- *sn* -- at each instance.
Lines 22 and 24, delete "myo" and insert -- *myo* -- therefor.
Lines 30-42, delete "myo", all occurences and insert -- *myo* -- at each instance.
Lines 30-42, delete "sn", all occurences and insert -- *sn* -- at each instance.

Signed and Sealed this

Seventh Day of September, 2004

JON W. DUDAS
*Director of the United States Patent and Trademark Office*

UNITED STATES PATENT AND TRADEMARK OFFICE
CERTIFICATE OF CORRECTION

PATENT NO.    : 6,737,536 B1
DATED         : May 18, 2004
INVENTOR(S)   : Rajindra Aneja It is certified that error appears in the above-identified patent and that said Letters Patent is hereby corrected as shown below:

Title page,
Item [56], References Cited, U.S. PATENT DOCUMENTS, delete "Anja" and insert -- Aneja --.

Column 1, line 1 through Column 24, line 45,
Change all occurrences of "myo" to -- *myo* --; and change all occurrences of "sn" to -- *sn* --.

Column 1,
Line 66, after "2-fatty acyl", delete "or".

Column 4,
Line 39, after "phosphonate", delete "tar".

Column 5,
Line 44, delete "myo-inositois" and insert -- *myo*-inositol --.

Column 9,
Line 3, delete "(5)" and insert -- (1) --.
Line 9, delete "1" from above and left of the structure.
Line 50, delete "5" underneath the structure and insert -- 1 --.
Line 60, delete "synthon" and insert -- synthons --.

Column 11,
Line 13, delete "1969a".

Column 12,
Line 35, delete "1969a".

Column 14,
Line 55, delete "1969a".

Column 16,
Line 9, delete "chioroacetyl" and insert -- chloroacetyl --.
Line 35, delete "pharmnacodynamnic" and insert -- pharmacodynamic --.
Line 36, delete "antuinflammatory" and insert -- antiinflammatory --.
Line 42, delete "1D-1-(l-stearoyl-2-eicosapenatenoyl-sn-glycero3-" and insert -- 1D-1-(1-stearoyl-2-eicosapentaenoyl-*sn*-glycero-3 --.

UNITED STATES PATENT AND TRADEMARK OFFICE
CERTIFICATE OF CORRECTION

PATENT NO. : 6,737,536 B1
DATED : May 18, 2004
INVENTOR(S) : Rajindra Aneja

It is certified that error appears in the above-identified patent and that said Letters Patent is hereby corrected as shown below:

Column 17,
Line 20, delete "eicosdienoyl- and" and insert -- eicosadienoyl- and --.

Column 23,
Line 25, delete "glycero-l", and insert -- glycero-3 --.

Columns 23 and 24,
Delete each occurrence of "myo" and insert -- *myo* --.
Delete each occurrence of "sn" and insert -- *sn* --.
Delete each occurrence of "O" and insert -- *O* --.

Signed and Sealed this

Twenty-seventh Day of December, 2005

JON W. DUDAS
*Director of the United States Patent and Trademark Office*

(12) EX PARTE REEXAMINATION CERTIFICATE (7407th)
United States Patent
Aneja

(10) Number: US 6,737,536 C1
(45) Certificate Issued: Mar. 16, 2010

(54) INOSITOLPHOSPHOLIPIDS AND ANALOGUES

(75) Inventor: Rajindra Aneja, Ithaca, NY (US)

(73) Assignee: Nutrimed Biotech, Ithaca, NY (US)

Reexamination Request:
No. 90/009,245, Aug. 8, 2008

Reexamination Certificate for:
Patent No.: 6,737,536
Issued: May 18, 2004
Appl. No.: 10/067,648
Filed: Feb. 4, 2002

Related U.S. Application Data

(60) Provisional application No. 60/266,433, filed on Feb. 5, 2001.

(51) Int. Cl.
*C07F 9/00* (2006.01)
*C07F 9/6561* (2006.01)
*C07F 9/117* (2006.01)

(52) U.S. Cl. .............................. 554/82; 554/79; 554/91
(58) Field of Classification Search ........................ None
See application file for complete search history.

(56) References Cited

PUBLICATIONS

The Echelon Product Catalog, 1998.
The Echelon Product Catalog, 1999.
Young et al., Total Synthesis of the Four Stereoisomers of Dihexadecanoyl Phosphatidylinositol and the Substrate Stereospecificity . . . , J Med. Chem. 1990, 33, 641–646.
Lewis et al., Substrate Requirements of Bacterial Phophatidylinositol–Specific Phospholipase C, Biochemistry, 1993, 32, 8836–8841.

*Primary Examiner*—Gary L Kunz

(57) ABSTRACT

This invention relates to inositolphospholipids, particularly to synthetic phosphatidyl-myo-inositols (PtdIns), ceramide-phophoinositols (CerPhosIns) and their structural and stereochemical analogues. The invention specifically provides a novel approach to synthesis of inositolphospholipids which is suitable for laboratory scale preparation as well as for large scale industrial production. The synthetic approach is applicable equally well for the preparation of inositolphospholipids carrying saturated lipid chains, unsaturated lipid chains with one or more double or triple bonds, chains with hydroxyl, amino and other functional groups, or combinations of these. In addition, it provides novel high purity diastereomer molecular species on inositolphospholipids that have unequivocally defined structure and absolute stereochemistry in both the myo-inositol and the glycerol residues and are obtainable only by the present new approach. The invention further provides methods for characterizing and using these high purity diastereomeric compounds.

US 6,737,536 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 8 is confirmed.

Claim 7 is determined to be patentable as amended.

New claim 9 is added and determined to be patentable.

Claims 1–6 were not reexamined.

7. A substantially single diastereomeric form of an inositolphospholipid prepared by the process of claim 1, *wherein the substantially single diastereomeric form of an inositolphospholipid has unequivocally defined structure and absolute stereochemistry in both the myo-inositol and the glycerol residues.*

*9. A substantially single diastereomeric form of an inositolphospholipid wherein said inositolphospholipid has the phosphatidyl-myo-inositol structure: 1D-1-(1-fattyacyl$^1$-2-fattyacyl$^2$-sn-glycero-3-phospho)-myo-inositol; 1D-1-(3-fattyacyl$^1$-2-fattyacyl$^2$-sn-glycero-1-phospho)-myo-inositol; 1L-1-(1-fattyacyl$^1$-2-fattyacyl$^2$-sn-glycero-3-phospho)-myo-inositol; or 1L-1-(3-fattyacyl$^1$-2-fattyacyl$^2$-sn-glycero-1-phospho)-myo-inositol; wherein fattyacyl$^1$ and fattyacyl$^2$ are identical or non-identical, and wherein the said substantially single diastereomeric form of an inositolphospholipid has unequivocally defined structure and absolute stereochemistry in both the myo-inositol and the glycerol residues.*

\* \* \* \* \*